United States Patent [19]

Dunn et al.

[11] Patent Number: 5,776,260
[45] Date of Patent: Jul. 7, 1998

[54] LIQUID WASTE DISPOSAL AND CANISTER FLUSHING SYSTEM AND METHOD

[75] Inventors: James L. Dunn; Timothy A. Carty, both of Topeka, Kans.

[73] Assignee: Dornoch Medical Systems, Inc., Riverside, Mo.

[21] Appl. No.: 698,940

[22] Filed: Aug. 16, 1996

[51] Int. Cl.$^6$ .................................................. B08B 9/08
[52] U.S. Cl. ........................... 134/18; 134/24; 134/26; 134/56 R; 134/57 R; 134/58 R; 134/116; 134/166 R; 134/169 R; 134/177; 134/186
[58] Field of Search .................. 134/56 R, 57 R, 134/58 R, 166 R, 177, 135, 104.2, 116, 150, 167 R, 168 R, 169 R, 22.1, 22.18, 24, 26, 18, 186

[56] References Cited

U.S. PATENT DOCUMENTS

| | | | |
|---|---|---|---|
| 1,693,885 | 12/1928 | Butterworth | 134/168 R |
| 1,827,085 | 10/1931 | Huff | 134/167 R |
| 2,641,270 | 6/1953 | Allen | 134/177 |
| 3,603,328 | 9/1971 | Fenn | 134/167 R |
| 3,780,757 | 12/1973 | Jordan | 134/169 R |
| 3,791,394 | 2/1974 | Hammelmann | 134/169 R |
| 3,897,599 | 8/1975 | Artzer | 134/168 R |
| 4,058,412 | 11/1977 | Knapp et al. | 134/104.2 |
| 4,905,325 | 3/1990 | Colditz | 134/166 R |
| 4,961,440 | 10/1990 | Wright | 134/167 R |
| 5,186,195 | 2/1993 | Wall | 134/166 R |
| 5,460,193 | 10/1995 | Levallois et al. | 134/181 |

FOREIGN PATENT DOCUMENTS

| 650678 | 3/1979 | U.S.S.R. | 134/167 R |
|---|---|---|---|

*Primary Examiner*—Frankie L. Stinson
*Attorney, Agent, or Firm*—Litman, McMahon & Brown, L.L.C.

[57] ABSTRACT

A liquid waste disposal and canister flushing system includes a cabinet with a sink for receiving the canister and a subsink for receiving a lower portion thereof. The subsink is connected to a drain line. A plunger subassembly includes a stopper which functions as a drain valve for the canister. An injection jet is connected to water and cleaning solution sources and discharges diluted cleaning solution into the canister for flushing same. The injection jet engages the plunger subassembly for ejecting the stopper from a canister drain opening. A control system includes a programmable microprocessor which can be programmed to provide drain and flush cycles of predetermined duration. A method of liquid waste disposal and canister flushing utilizes the microprocessor for delaying the flush cycle until completion of the drain cycle. The control system can provide drain and flush cycles of predetermined durations.

36 Claims, 9 Drawing Sheets

LIQUID WASTE DISPOSAL AND CANISTER FLUSHING SYSTEM AND METHOD

BACKGROUND OF THE INVENTION

I. Field of the Invention

The present invention relates generally to liquid waste disposal and canister flushing, and in particular to the disposal of liquid medical waste from containers which are flushed in preparation for reuse.

II. Description of the Related Art

Various forms of liquid waste are commonly encountered in a variety of different situations. For example, liquid medical wastes are commonly produced in surgery and other medical procedures. Such wastes can include blood and other body fluids of patients, and major surgery can produce a number of containers of such waste from a single patient. Liquid medical waste generates significant disposal problems due to its possible contamination with various infectious diseases, including AIDS, hepatitis, MRSA and tuberculosis. In an effort to combat the risks associated with handling such liquid medical wastes and to protect medical personnel from the spread of infectious diseases, disposal procedures have become increasingly complicated and expensive.

One type of disposal procedure for liquid medical wastes involves emptying the waste canisters from surgery into specially designed plumbing fixtures. However, this procedure can involve risks associated with splashback and aerosolization whereby medical personnel can be exposed to the waste and bacteria present therein.

Another type of procedure involves the centralized collection of the waste with specially designed equipment having a liquid waste reservoir that must periodically be dumped. Such equipment is generally relatively expensive and can add significantly to the cost of equipping a hospital operating room or other treatment facility. Yet another method of disposing of liquid medical waste involves mixing it with a solidifying agent in the container. The medical waste in the container then disposed of pursuant to regulations governing the disposal of biohazardous waste. The disadvantages with this disposal method include the cost of the canister, which becomes a single-use item, and the extra charges for disposing of biohazardous waste, which is sometimes referred to as "red bag" waste.

Liquid medical waste disposal procedures can come under rules and regulations imposed by various governmental and regulatory agencies, including the Occupational Safety and Health Administration (OSHA), the Food and Drug Administration (FDA), and the Center for Disease Control (CDC).

Heretofore there has not been available a liquid medical waste disposal system and method with the advantages and features of the present invention.

SUMMARY OF THE INVENTION

In the practice of the present invention, a liquid waste disposal and canister flushing system is provided which includes a cabinet forming a sink for receiving the canister and a subsink for receiving a lower portion of the container. The subsink is connected to a drain line. The canister includes a lid with an accessory opening, a base with a drain opening, and a sidewall connected to the lid and to the base. With a lower portion of the canister received in the subsink, the canister base is positioned above a bottom of the subsink. A plunger assembly includes a stopper positioned in the canister base drain opening for closing same and a rod with a lower end connected to the stopper and an upper end positioned in the canister lid accessory opening. An injection jet is connected by water and cleaning solution lines to water and cleaning solution sources and mixes water and cleaning solution to form a diluted cleaning solution which is discharged therefrom into the canister. The injection jet is inserted in the canister lid accessory opening where it engages the plunger subassembly rod upper end and ejects the stopper into the subsink, thus opening the drain valve and permitting the liquid waste contents of the canister to drain into the subsink and then into the drain line. When the drain cycle is complete, the diluted cleaning solution is discharged from the injection jet into the canister for flushing same. A control system is provided for sequencing the drain and flush cycles whereby the flush cycle does not commence until the drain cycle is complete. The control system can include a programmable microprocessor which allows the drain and flush cycle durations to be adjusted, provides visual and audio indications of the status of the system in operation and which prevents flushing until the canisters are enclosed in the sink with a lid of the cabinet closed. A method of disposing of liquid waste and flushing a canister containing same is also provided and consists of the steps of draining the canister for a predetermined time prior to commencement of a flush cycle and flushing the canister for a predetermined time interval corresponding to a flush cycle.

OBJECTS AND ADVANTAGES OF THE INVENTION

The principal objects and advantages of the present invention include: providing a liquid waste disposal and canister flushing system; providing such a system which facilitates the relatively inexpensive disposal of medical waste; providing such a system which facilitates reuse of medical waste containers; providing such a system which is relatively easily adapted for use with existing medical waste containers; providing such a system which reduces the splashing of medical waste being disposed; providing such a system which can reduce the hazards associated with handling and disposing of medical waste; providing such a system which facilitates the discharge of medical waste into a sewer system as non-hazardous waste; providing such a system which can reduce the amount of disposable components associated with medical waste disposal; providing such a system which provides effective neutralization of various bacteria and infection sources; providing such a system which is usable by medical personnel with relatively little training; providing such a system with a control system which is at least partially automated; providing such a system which is relatively portable; providing such a system which is relatively compact; providing such a system which can be installed with relatively simple plumbing and electrical connections; providing such a system which is economical to manufacture and use, efficient in operation, capable of a long operating life and generally well adapted for the proposed usage thereof; providing a liquid medical waste disposal and canister flushing method; providing such a method which is relatively efficient; providing such a method which is relatively safe; providing such a method which is relatively economical and providing such a method which is particularly well adapted for the proposed usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

Figure 1:
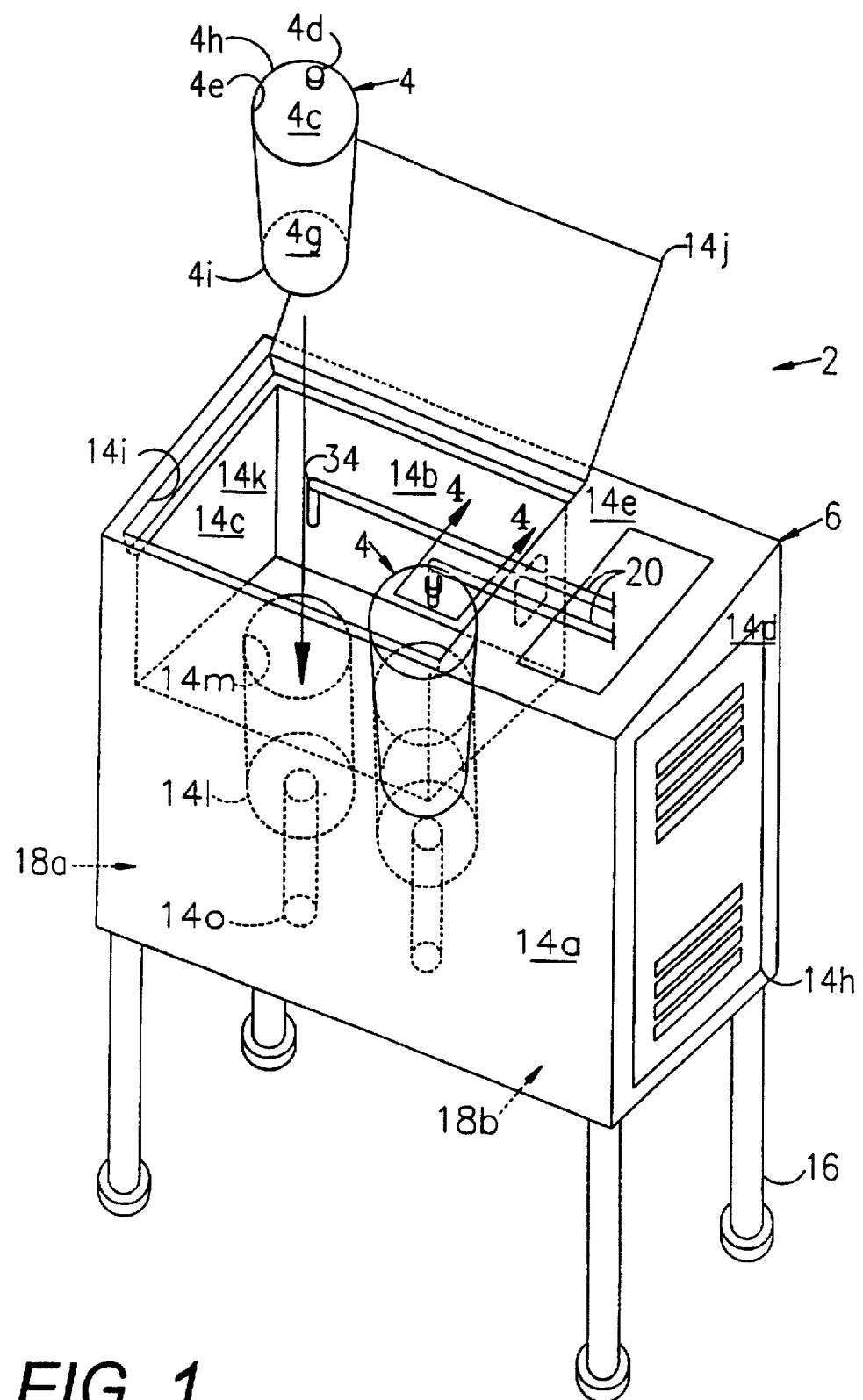
FIG. 1 is an upper, front perspective view of a liquid medical waste disposal and canister flushing system embodying the present invention.
Figure 2:
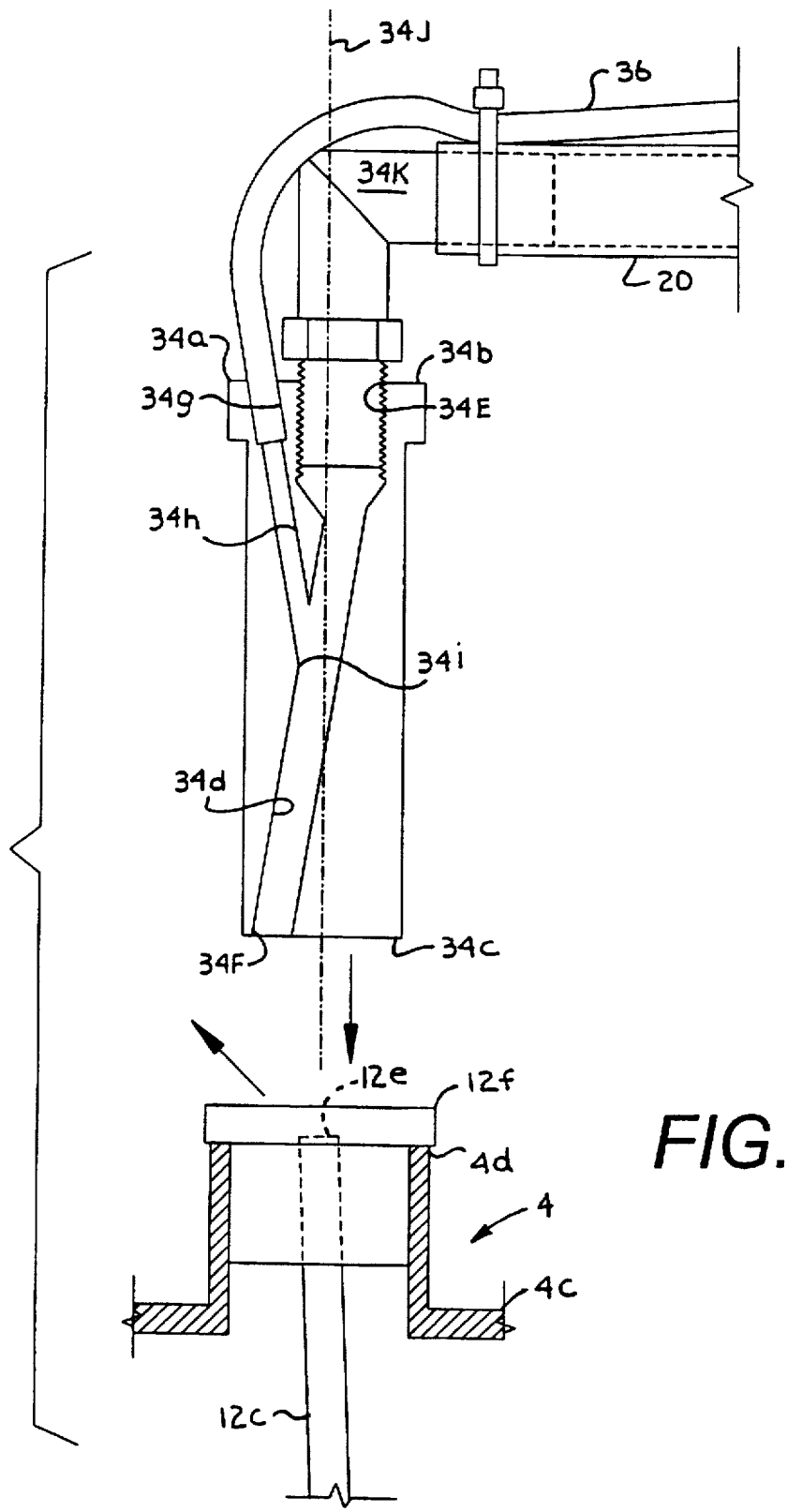
FIG. 2 is an enlarged, fragmentary, vertical cross-sectional view thereof.
Figure 3:
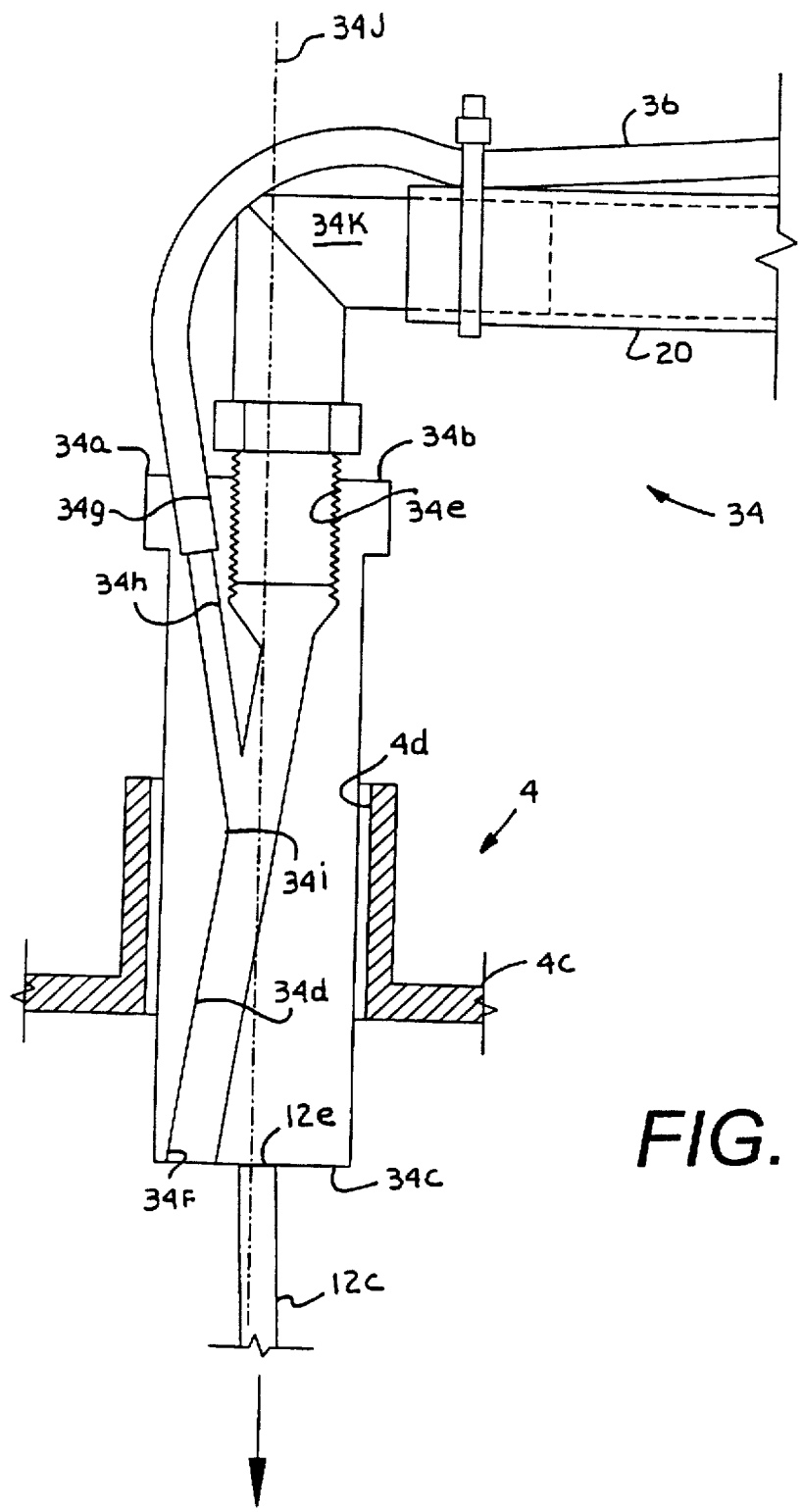
FIG. 3 is an enlarged, fragmentary, vertical cross-sectional view thereof, showing an injection jet being inserted into a canister lid and dislodging a plunger subassembly.
Figure 4:
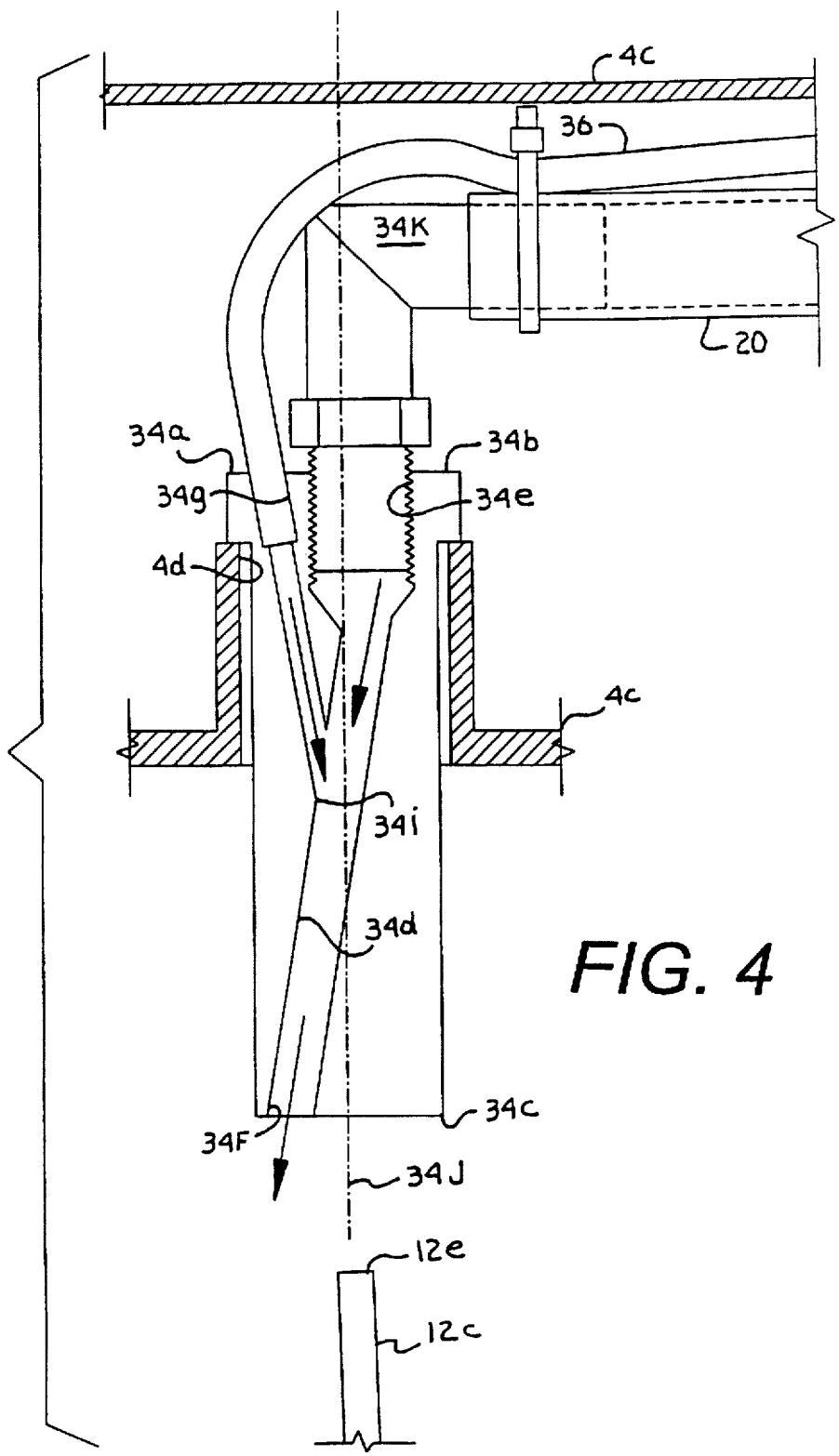
FIG. 4 is an enlarged, fragmentary, vertical cross-sectional view thereof, taken generally along line 4—4 in FIG. 1 and showing an injection jet inserted in the lid of one of the canisters.
Figure 5:
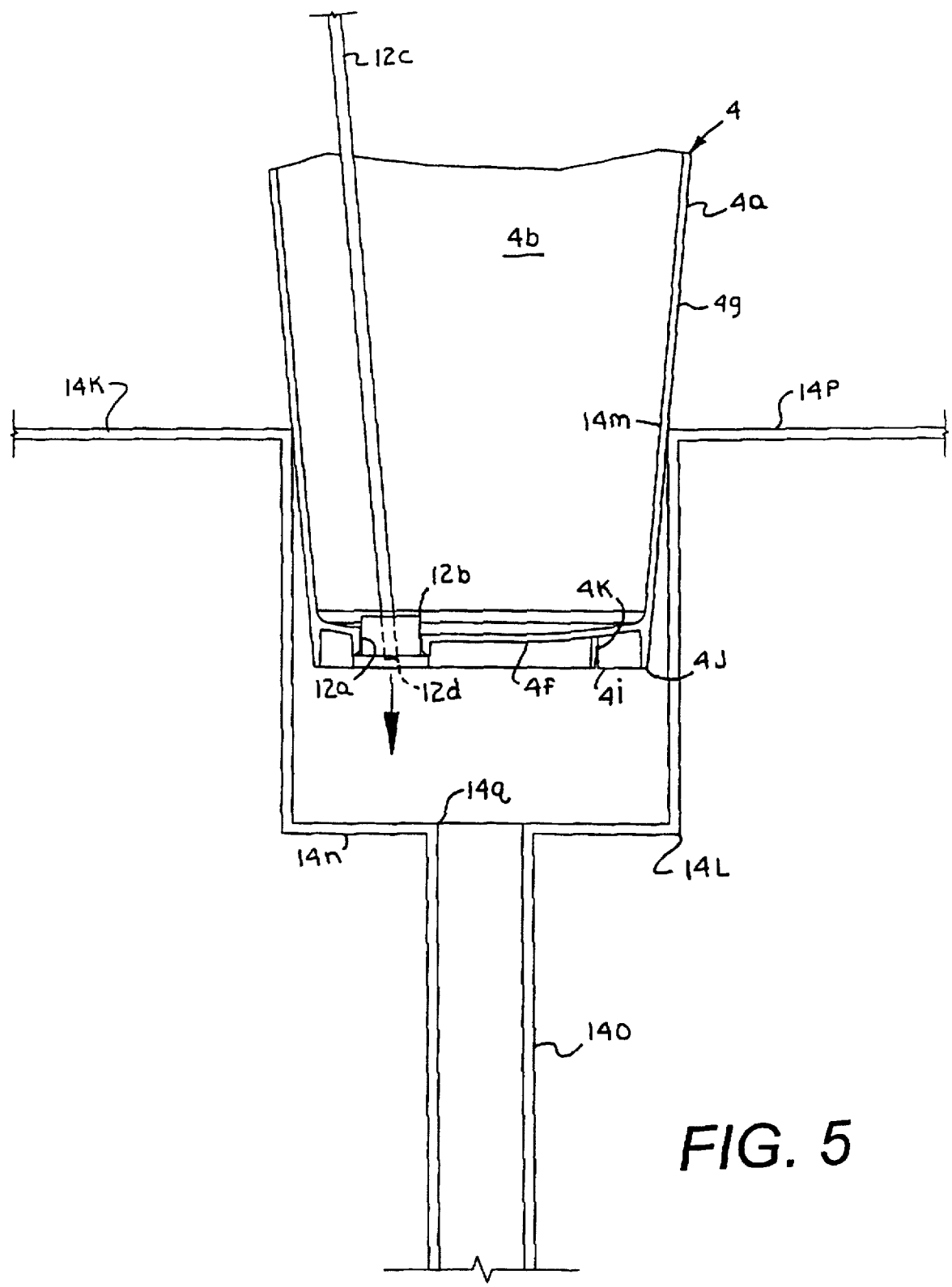
FIG. 5 is an enlarged, fragmentary, vertical cross-sectional view thereof, generally showing a lower end of the canister positioned in a subsink with the plunger subassembly in a closed position.
Figure 6:
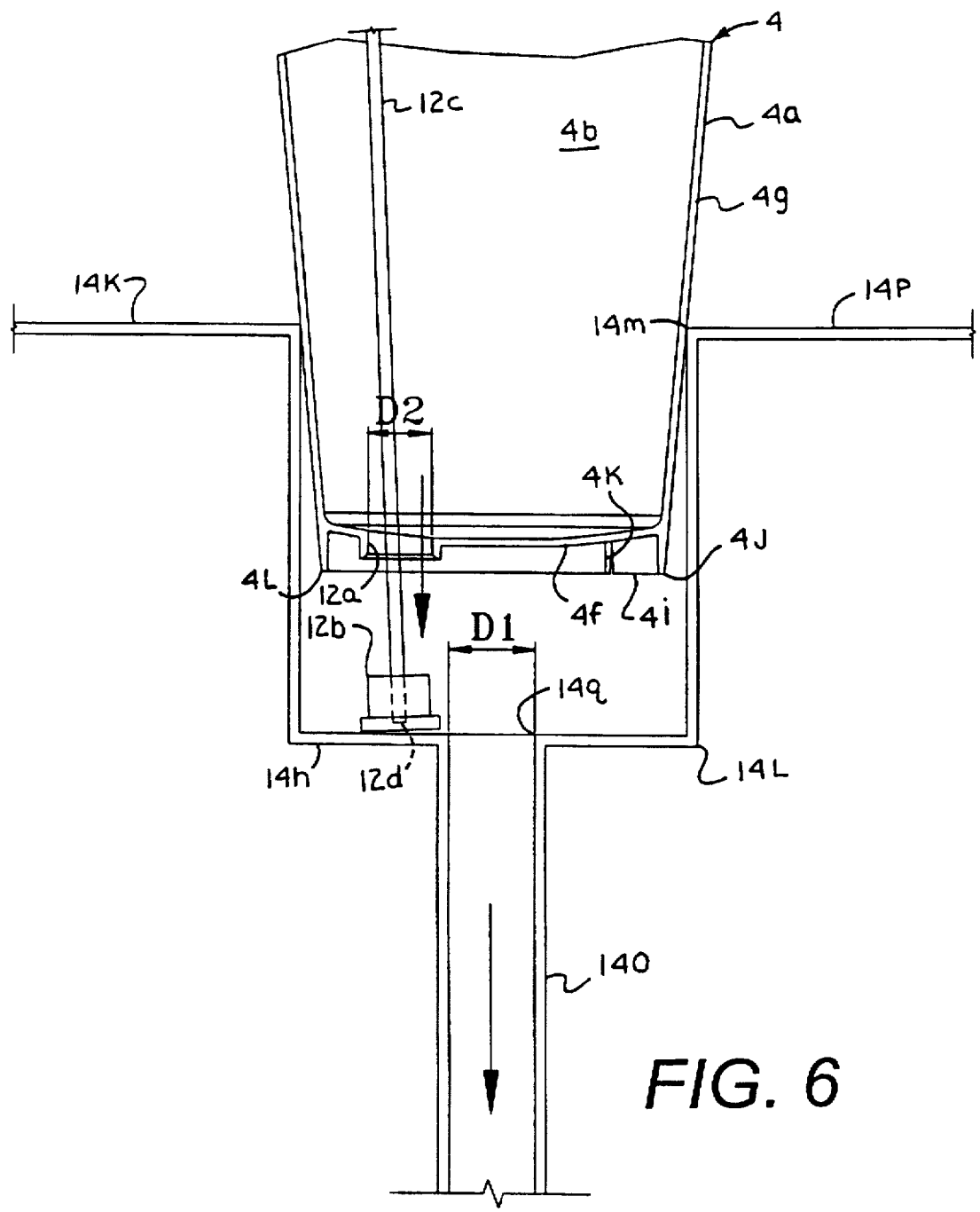
FIG. 6 is an enlarged, fragmentary, vertical cross-sectional view thereof, generally showing a plunger subassembly in an open, drain position.
Figure 7:
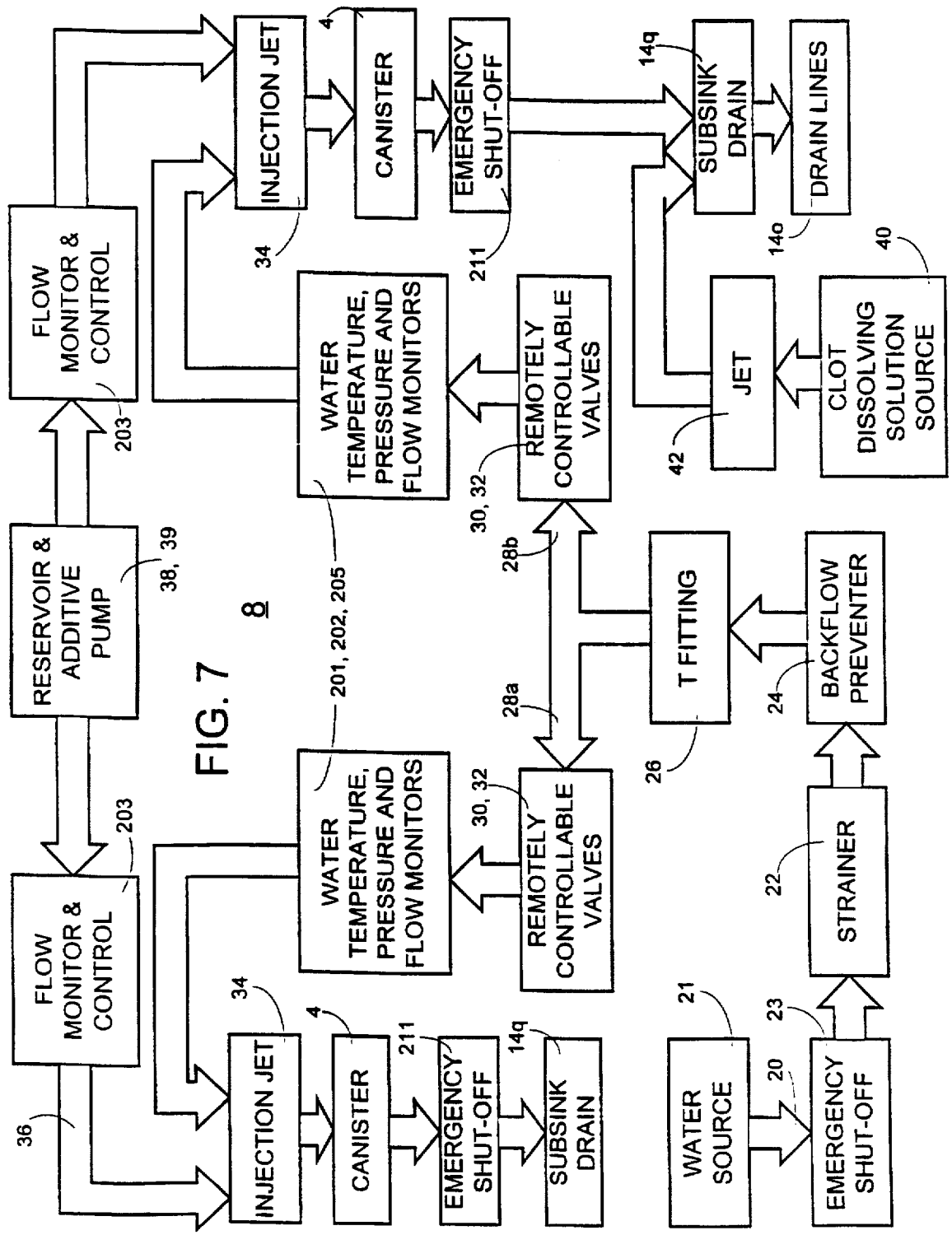
FIG. 7 is a schematic diagram of a plumbing system thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 2 generally designates a liquid medical waste disposal and canister flushing system embodying the present invention. Without limitation on the generality of useful applications of the system 2, it is designed for operation on modified medical waste canisters 4. The system 2 generally comprises a cabinet 6, a plumbing system 8 and a control system 10.

II. CANISTER 4

An exemplary application of the disposal and flushing system 2 is with a canister 4 of the type which is commonly used in surgery for medical waste generally comprising the patient's blood and other fluids. A typical such canister is available from Allied Healthcare Products, Inc. of St. Louis, Mo. and includes a body 4a forming a receptacle 4b of predetermined volume (e.g. 2550 milliliters) and a releasable lid 4c which is preferably upwardly-convex to prevent the pooling of fluids thereon. The body 4a includes upper and lower ends 4h,i. The lid 4c can be secured to the body 4a with a Leur lock-type connection and can include suitable inlet ports, fittings for vacuum lines, check valves, clamps, etc. The lid 4c includes an accessory port 4d with a generally cylindrical, tubular configuration and an open mouth 4e. The canister 4 further includes a base 4f, which is generally circular, and a frusto-conical sidewall 4g which converges downwardly in a tapering configuration to permit nesting of canister bodies 4a.

The canister 4 described thus far is a relatively standard configuration. For use with the system 2 of the present invention, the standard canister 4 is modified to include a plunger subassembly 12 for which a drain opening 12a is formed off-center in the canister base 4f and selectively receives a stopper 4b in sealing engagement. The canister base 4f is provided with a configuration which is concave from the inside of the canister and to facilitate drainage through the drain opening 12a, which opens at approximately the lowest level of the concave base 4f. A canister bottom flange or lip 4j extends downwardly from the canister base 4f and comprises an extension of the canister sidewall 4g. A plurality of drain notches 4k are formed in the bottom lip 4j and cooperate with the concave configuration of the canister base 4f whereby water will drain from the canister base 4f with the canister 4 in an inverted position, for example, when automatic dishwashing equipment is used for washing the canisters 4 in inverted positions.

A plunger rod 12c includes a lower end 12d embedded in the stopper 12b and an upper end 12e protruding into the accessory port 4d and mounting an upper cap 12f which is received in and is adapted to selectively close the accessory port 4d. In addition to the plunger subassembly 12 shown, other drain valve means can be utilized with the canister 4. These can include, for example, a variety of caps, lids, plugs and spring loaded devices for selectively opening and closing a drain opening formed in either the canister base 4f or the canister sidewall 4g.

III. CABINET 6

The cabinet 6 includes front and back panels 14a,b; first and second side panels 14c,d; and a top 14e. The second side 14d has an opening which is selectively covered by a side access panel 14h. A top opening 14i is selectively covered by a lid 14j hingedly mounted on the top panel 14e. The top opening 14i provides access to a sink 14k. A pair of subsinks 14l with open, upper mouths 14m and subsink bottoms 14n depend downwardly from a floor 14p of the sink 14k. The subsinks 14l are generally cylindrical. Although two subsinks 14l are shown, the system 2 could include a single subsink 14l or more than two subsinks 14l. The subsinks 14l communicate through subsink drain openings 14q in their bottoms 14n with subsink drain lines 14o comprising the plumbing discharge subsystem 8b. The cabinet 6 is provided with adjustable-length legs 16 for leveling. An interior 18 of the cabinet 6 generally forms a sink chamber 18a and a control chamber 18b.

IV. PLUMBING SYSTEM 8

The plumbing system 8 generally includes a supply subsystem 8a and a drain subsystem 8b. The supply subsystem 8a includes a water inlet line 20 connected to a suitable pressurized water source 21, such as the normal municipal water service, a water tank or a water pump. A strainer 22 is provided in the water inlet line 20 and a backflow preventer valve 24 is provided downstream therefrom. The water inlet line 20 connects to a T-fitting 26, forming first and second supply branches 28a,b.

Each supply subsystem branch 28a,b includes a gate-type shut-off valve 30 and a solenoid-actuated valve 32 in line therewith. Each water inlet line 20 terminates in an injection jet 34, which also communicates with a cleaning solution injection line 36 communicating with a cleaning solution source 38, which can include a pump for pumping the cleaning solution under pressure to the injection jet 34.

Each injection jet 34 includes a generally cylindrical body 34a with a flanged upper end 34b and a lower end 34c. A jet passage 34d extends downwardly from a threaded water inlet port 34e located off-center in the upper end 34b. The water inlet line 20 is connected to the water inlet port 34e by an elbow 34k. A discharge orifice 34f is located in the body lower end 34c, and is also off-center whereby the jet passage 34d is skewed with respect to a longitudinal axis 34j of the injection jet body 34a. Due to the skewed, angular orientation of the jet passage 34d, diluted cleaning solution therefrom is directed generally at the canister sidewall 4g, creating a swirling flushing action in the canister receptacle 4b. A cleaning solution inlet port 34g is formed in the body upper end 34b and communicates with a cleaning solution passage 34h which forms a Y-intersection 34i with the jet passage 34d in an interior part of the body 34a. The cleaning solution inlet port 34g is connected to the cleaning solution line 36.

A venturi effect is created by passage of water through the jet passage 34d whereby cleaning solution is drawn through the cleaning solution passage 34h for combining with water to form the diluted cleaning solution mixture which is discharged through the discharge orifice 34f.

An optional clot-dissolving solution source 40 communicates with a drain line jet 42 directed into the drain line 14o and functions to dissolve blood clots therein. Although the clot-dissolving solution source 40 and the jet 42 are optionally shown on the second plumbing system branch 28b, they could be provided on the first branch 28a as well, or eliminated all together whereby clots in the drain line 14o could be dealt with manually.

V. CONTROL SYSTEM 10

The control system 10 utilizes a control microprocessor 50. A program port 52 provides input access to the microprocessor 50 through a suitable RAM device 53a. A ROM device 54 is also connected to the microprocessor 50.

Analog-to-digital input conversion capabilities are provided by an A\D convertor 56 which is connected to an encoder 58, which in turn is connected to the microprocessor 50 through a RAM device 53b. A selection key 60 also provides digital input to the encoder 58. A level probe 62 is connected to the solution source 38 for monitoring the level therein and is connected to the RAM device 53b through an amplifier 62a and an A\D convertor 56b.

A solenoid valve control 64 includes a digital output module 64a which is connected to the solenoid valves 32 and to a pair of indicator lights 64b for indicating the open or closed positions of the solenoid valves 32. The digital output module 64a is connected to the microprocessor 50 through a RAM device 53c.

A display device 66 is mounted on the cabinet top panel 14e and is connected to the microprocessor 50 through a RAM device 53d and a driver 66a and can comprise, for example, an LED display for indicating the state of the control system 10 or various functions thereof, such as time remaining to complete a flush cycle, delay mode (as explained in more detail below), etc.

Figure 8:
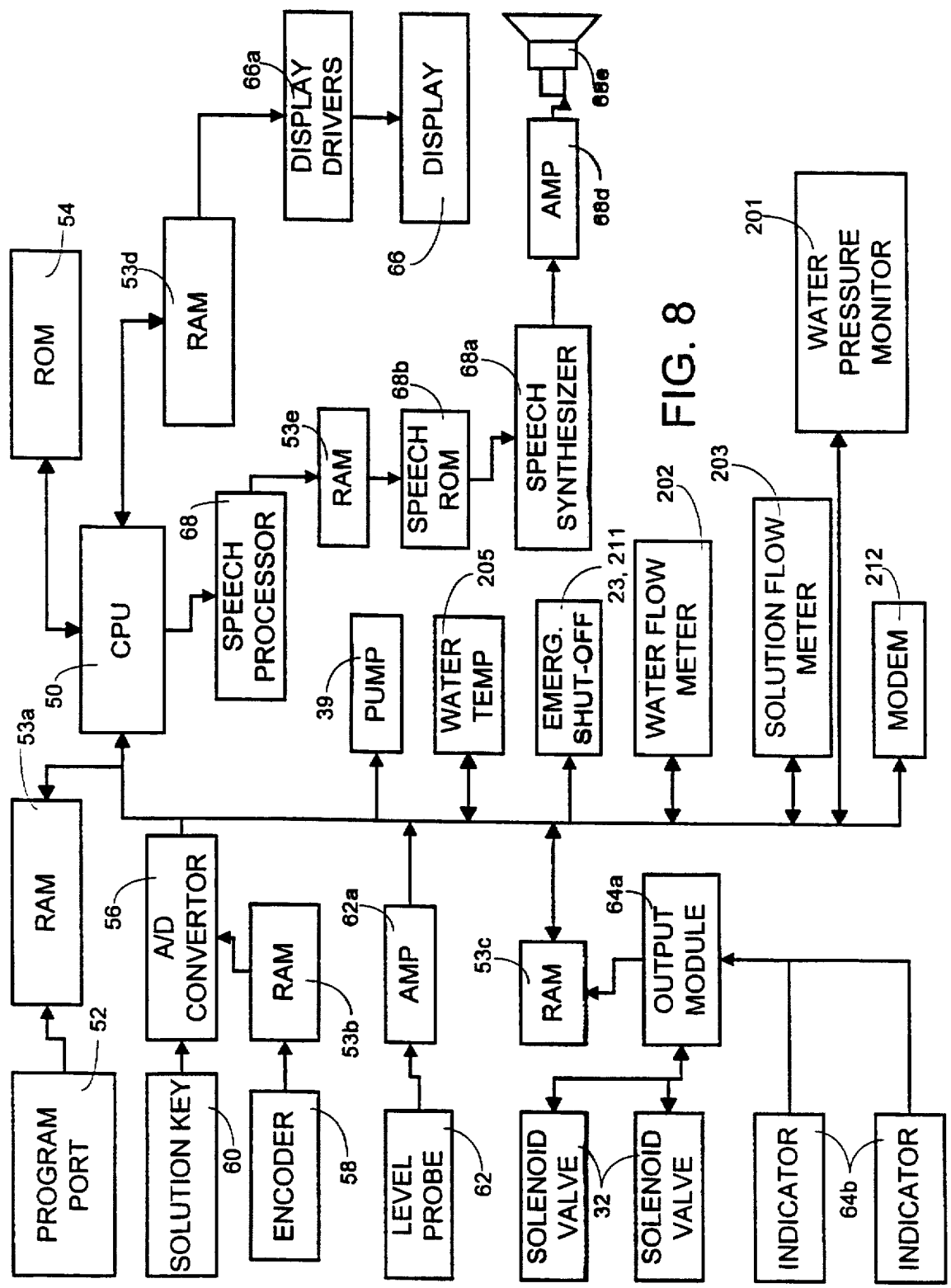
FIG. 8 is a schematic diagram of a control system thereof.

A voice enunciation subsystem 68 includes a speech processor 68a connected to the microprocessor 50, a RAM device 53e, a speech ROM device 68b, a speech synthesizer 68c, an amplifier 68d and a suitable output device, such as a speaker 68e, all suitably interconnected as shown in FIG. 8.

It will be appreciated that the control system 50 can comprise various alternative configurations with appropriate analog, digital or analog/digital components for controlling various functions of the system 2. In particular, other inputs and outputs could be provided for monitoring various functions of the system 2 and for automating same to a greater or lesser degree.

VI. OPERATION AND LIQUID MEDICAL WASTE DISPOSAL AND CANISTER FLUSHING METHOD

Figure 9:
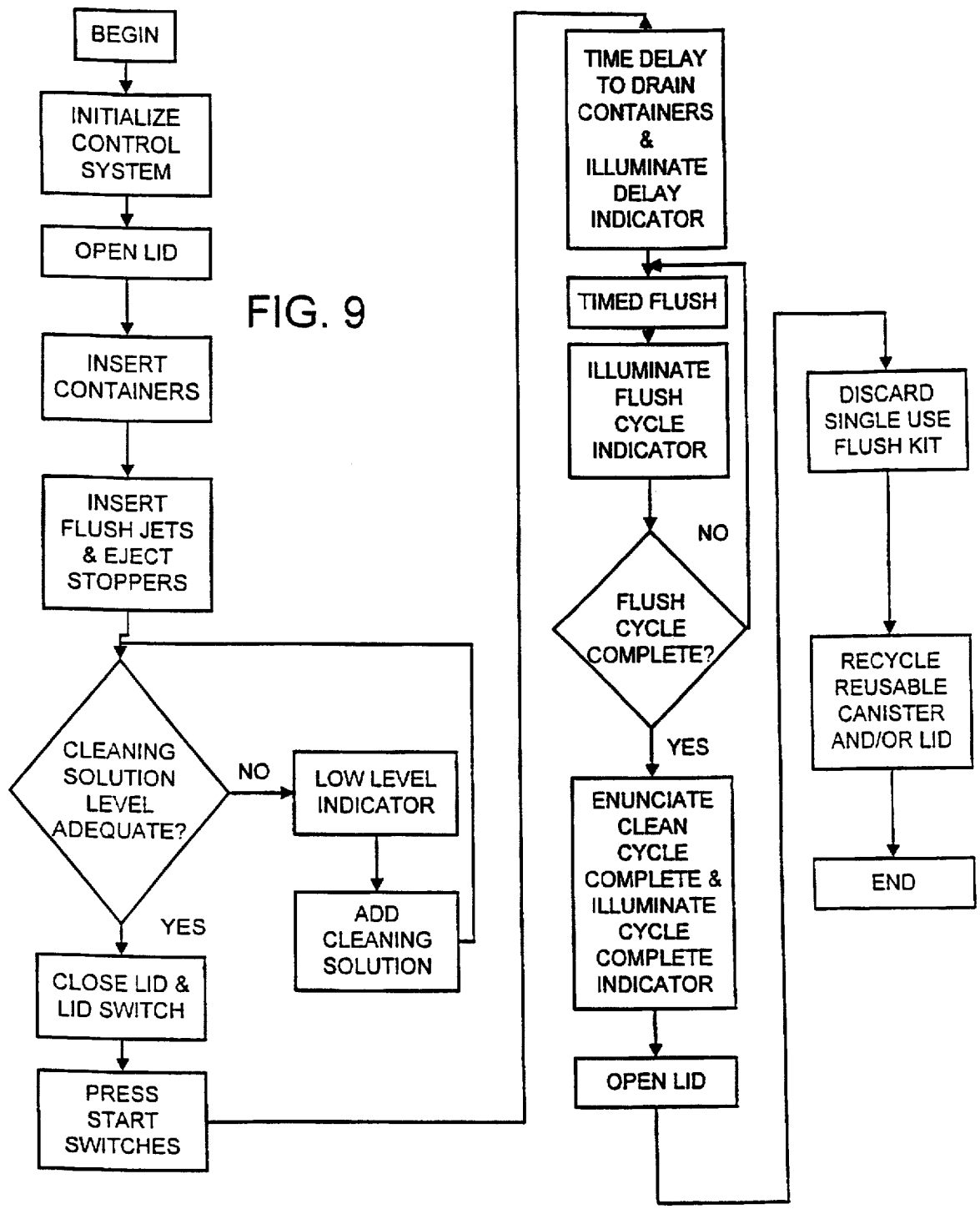
FIG. 9 is a flow chart of a method of liquid waste disposal and canister flushing embodying the present invention.

FIG. 9 comprises a flow chart showing a method of disposing of liquid medical waste and flushing the canisters 4.

The control system 10 is initialized, for example, by programming the microprocessor 50 with appropriate operating parameters including delay or drain cycle times, flush cycle times, etc. The cabinet lid 14j is opened to access the sink 14k. One or two canisters 4 are placed in respective subsinks 14l, which have circular mouths 14m with diameters intermediate the diameters of the canister lids 4c and bases 4f whereby the canisters 4 extend partway into the subsinks 14l and the canister sidewalls 4g form friction fits with the subsink mouths 14m whereby a friction seal is formed around the circumference of the canister sidewalls 4g.

The injection jets 34 are next connected by removing the caps 12f from the plunger subassemblies 12 to provide access to the canister lid accessory ports 4d wherein the injection jet body lower ends 34c engage the plunger rod upper ends 12e. Pushing the injection jet bodies 34a into the canister lid accessory ports 4d dislodges the plunger stoppers 12d from the canister base drain openings 12a whereby the canisters 4 drain their contents into the subsinks 14l. The cabinet subsink drain openings 14q are sized larger with diameters D1 than the canister base accessory openings 12a with diameters D2 whereby the liquid medical waste from the canisters 4 is substantially instantly drained from the subsinks 14l. In other words, the subsinks 14l have greater flow discharge rate capacities than the canisters 4 whereby backing up of medical waste within the subsinks 14l is avoided.

With the injection jets 34 placed in the canister lid accessory ports 4d, the cabinet lid 14j can be closed, which permits the flush cycles to be commenced or initiated by pressing the start buttons. The cabinet lid 14j can be positioned sufficiently close to the injection jets 34 that the latter are retained in place in the canister lid accessory ports 4d by the cabinet lid 14j during the flush cycle. A timed delay of the commencement of the flush cycle is provided after the cabinet lid 14j is closed and the start buttons are actuated, which delay permits substantially complete drainage of the canisters 4 through the subsinks 14l before the flush cycle commences. Thus, the flush cycle is initiated in substantially empty canisters 4. The microprocessor 50 can be programmable to vary the timed delay for canister draining and for the length of the flush cycle.

As a general guideline, it is desirable to flush the canisters 4 with a volume of solution equal to approximately 6 times their capacities. The cleaning solution mixture preferably comprises water and a suitable agent for killing virus and bacteria. For example, sodium hypochlorite (i.e., bleach) in a solution of about 1200 to 1400 parts per million with water has generally been found to be suitable. A delay of approximately 8 seconds has been found to be sufficient to drain the canisters 4, and a flush cycle of approximately 45 seconds has generally been found to be sufficient.

The solution mixture is preferably chosen to meet the particular objectives of a disposal and flushing system. For example, disinfection and flushing are generally the primary objectives with liquid medical waste containers 4, which for most reuse purposes do not have to be cleaned to the point where they would be considered sterile, since sterility is normally not required for liquid medical waste canisters. The plunger subassemblies 12 and the canister lids 4c can be disposed of and the container bodies 4a reused at a fraction of the cost of disposing of complete canisters 4 full of liquid medical waste. The lids 4c and the plunger subassemblies 12 would generally be considered "white" trash in medical facilities due to relatively low concentrations of liquid medical waste thereon and thus would not be subjected to the more stringent requirements typically in place for handling and disposing of the actual liquid medical wastes.

The flushed liquid medical waste from the system 2 would mix with the effluent from the medical facility in its plumbing drainage system and could normally be discharged into a municipal sewer system at levels well below the maximums permitted for medical waste effluents.

It is to be understood that while certain forms of the present invention have been illustrated and described herein, it is not to be limited to the specific forms or arrangement of parts described and shown.

What is claimed and desired to be secured by letters patent is as follows:

1. A liquid medical waste disposal and canister flushing system for a canister having a lid with an accessory port, a base and a drain opening, which system comprises:
   (a) a cabinet including a receptacle means for receiving at least a lower portion of the canister and the liquid waste contents thereof;
   (b) drain valve means associated with said drain opening and having open and closed positions respectively opening and closing said drain opening;
   (c) drain valve actuating means for opening said drain valve; and
   (d) an injection jet selectively received in said accessory port and including an upper end with an inlet port, a lower end with a discharge orifice and a jet passage extending between said inlet port and said discharge orifice, said discharge orifice being directed into said canister, said drain valve actuating means being engaged by said injection jet when it is received in said accessory port to open said drain valve.

2. The system according to claim 1, which includes:
   (a) said cabinet having a sink for receiving the canister and the sink having a subsink including said receptacle means.

3. The system according to claim 1, which includes a plunger subassembly having:
   (a) a stopper comprising said drain valve means; and
   (b) a plunger subassembly rod having a lower end connected to said stopper and an upper end and comprising said drain valve actuating means.

4. The system according to claim 1 wherein:
   (a) said canister includes a sidewall with said drain opening therein.

5. The system according to claim 1 wherein:
   (a) said canister base has a configuration which is concave from an interior of said canister and includes said drain opening therein.

6. A liquid waste disposal and canister flushing system for a canister including a lid with an accessory port, a base with a drain opening and a frusto-conical sidewall connected to the lid and the base, which system is connected to water and cleansing solution sources and comprises:

(a) a cabinet including:
      1) a sink receiving the canister and having a sink floor;
      2) a subsink having a mouth open at the sink floor and a subsink bottom positioned below the level of said sink floor; and
      3) said subsink at least partially receiving the canister with the subsink mouth engaging the canister sidewall;
   (b) a plunger subassembly including:
      1) a stopper having a closed position in said drain opening closing same and an open position in said subsink below said container base; and
      2) a rod having a lower end connected to said stopper and an upper end positioned within said accessory port with said stopper in its open position;
   (c) a water inlet line connected to the water source;
   (d) a cleaning solution line connected to the cleaning solution source;
   (e) an injection jet including:
      1) a body with upper and lower ends;
      2) a longitudinal axis;
      3) a water inlet port located at said upper end off-center with respect to said longitudinal axis;
      4) a cleaning solution inlet port located at said upper end off-center with respect to said longitudinal axis;
      5) a discharge orifice located at said lower end off-center with respect to said longitudinal axis;
      6) a jet passage extending between and open at said water inlet port and said discharge orifice, said jet passage being angularly skewed with respect to said longitudinal axis; and
      7) a cleaning solution inlet passage extending from said cleaning solution inlet port to said jet passage; and
   (f) a control system including:
      1) a microprocessor;
      2) a valve in said water inlet line, said microprocessor being connected to said valve for actuating same; and
      3) said microprocessor including flush cycle duration control means for controlling a duration of said flush cycle by means of said water valve.

7. The system according to claim 6 wherein said control system includes:
   a) delay means for delaying said flush cycle until a drain cycle is completed wherein said canister liquid waste contents are received in and drained from said subsink.

8. A method of disposing liquid waste from a canister having a lid with an accessory port, a base with a drain opening and a canister sidewall connected to the canister lid and canister base, which comprises the steps of:
   (a) providing the canister with a drain valve closing the drain opening and a drain valve opening mechanism;
   (b) inserting an injection jet into the accessory port and simultaneously operating the drain valve opening mechanism to open the drain valve;
   (c) draining the canister waste contents; and
   (d) flushing the canister via the injection jet.

9. The method according to claim 8, which includes the additional steps of:
   a) providing a cabinet with a receptacle;
   b) placing at least a lower portion of the canister in the receptacle; and
   c) draining the canister liquid waste contents into the receptacle.

10. The method according to claim 8, which includes the additional steps of:

(a) providing a water source;

(b) providing the injection jet with a water inlet port and a discharge orifice;

(c) providing a water inlet line;

(d) connecting the water inlet line to the water source and to the injection jet water inlet port; and (e) said flushing step includes the step of providing a water stream from said water source through said water line, through said injection jet and out of said discharge orifice into said canister.

11. The method according to claim 10, which includes the additional steps of:

(a) providing a stopper as the drain valve with the stopper being positionable in the drain opening;

(b) providing a plunger rod as the drain valve opening mechanism with said plunger rod including a lower end connected to the stopper and an upper end positioned in the accessory port with the closed stopper positioned in the drain opening; and (c) said drain valve opening mechanism operating step includes engaging said rod upper end with said injection jet, pushing said rod downwardly and ejecting said stopper from said drain opening as said injection jet is inserted in said accessory port.

12. The method according to claim 8, which includes the additional steps of:

(a) reusing said canister; and (b) discarding said canister lid sail drain valve operating mechanism and said drain valve.

13. The method according to claim 8, which includes the additional step of:

(a) delaying the step of flushing the canister a predetermined length of time after commencing the step of draining the canister.

14. A method of disposing of liquid waste from a canister having a lid with a accessory port, a base with a drain opening and a sidewall connected to the lid and the base, which includes the steps of:

a) providing a cabinet with a sink having a sink floor;

b) providing a subsink with a mouth open at the sink floor and a subsink bottom having a subsink drain opening in spaced relation below the sink mouth;

c) providing a plunger subassembly with a stopper in said canister drain opening and a rod with a lower end connected to the stopper and an upper end in the canister lid discharge opening;

d) connecting a drain line to the subsink drain opening;

e) placing a lower portion of the canister within the subsink with the subsink mouth engaging the canister sidewall and the canister base in spaced relation above the subsink bottom;

f) providing a water source;

g) providing a cleaning solution source;

h) providing an injection jet with a body having an upper end with a water inlet port connected to said water source and a cleaning solution inlet port connected to said cleaning solution source and a lower end with a discharge orifice;

i) providing a jet passage within said body from said water inlet port to said discharge orifice;

j) providing a cleaning solution passage within said body from said cleaning solution inlet port to said jet passage;

k) inserting said injection jet body into said discharge opening;

l) engaging said rod upper end with said injection jet body lower end;

m) ejecting said stopper from said canister drain opening and into said subsink;

n) draining said liquid waste from said canister into said subsink and into said drain line;

o) injecting water from said water source into said injection jet;

p) drawing cleaning solution from said cleaning solution passage into said jet passage by venturi action;

q) discharging diluted cleaning solution from said discharge orifice into said canister;

r) draining said diluted cleaning solution from said canister into said subsink and into said drain line;

s) providing a control system with a microprocessor; and t) delaying said flush cycle until said drain cycle is complete.

15. A liquid waste disposal and canister flushing system for a canister having a lid with an accessory port, a base and a drain opening, which system comprises:

(a) a cabinet including a receptacle means for receiving at least a lower portion of the canister and the liquid waste contents thereof;

(b) drain valve means associated with said drain opening and having open and closed positions respectively opening and closing said drain opening;

(c) drain valve actuating means for opening said drain valve;

(d) an injection jet selectively received in said accessory port and including an upper end with an inlet port, a lower end with a discharge orifice and a jet passage extending between said inlet port and said discharge orifice, said discharge orifice being directed into said canister;

(e) said cabinet having a sink for receiving the canister and the sink having a subsink including said receptacle means;

(f) said sink having a sink floor;

(g) said subsink having a mouth open at said sink floor and a subsink bottom; and (h) a drain communicating with said subsink bottom.

16. The system according to claim 15, which includes:

(a) said plunger subassembly having a generally cylindrical and engaging said canister at said subsink mouth with said canister base in spaced relation above said subsink bottom.

17. The system according to claim 15, which includes:

(a) drain line jet means associated with said sink drain; and (b) liquid clot-dissolving source means connected to said drain line jet means for supplying clot-dissolving liquid thereto.

18. A liquid waste disposal and canister flushing system for a canister having a lid with an accessory port, a base and a drain opening, which system comprises:

(a) a cabinet including a receptacle means for receiving at least a lower portion of the canister and the liquid waste contents thereof;

(b) drain valve means associated with said drain opening and having open and closed positions respectively opening and closing said drain opening;

(c) drain valve actuating means for opening said drain valve;

(d) an injection jet selectively received in said accessory port and including an upper end with an inlet port, a lower end with a discharge orifice and a jet passage extending between said inlet port and said discharge orifice, said discharge orifice being directed into said canister;

(e) a body with upper and lower ends;

(f) a water inlet port at said upper end;

(g) a cleaning solution inlet port at said upper end;

(h) a discharge orifice at said lower end;

(i) a jet passage extending from said water inlet port to said discharge orifice; and (j) a cleaning solution passage extending from said cleaning solution inlet port to said jet passage and forming an intersection therewith.

19. The system according to claim 18 wherein:

(a) said injection jet body has a longitudinal axis;

(b) said water inlet port and said discharge orifice are displaced from said longitudinal axis; and (c) said jet passage is skewed with respect to said longitudinal axis.

20. The system according to claim 18, which includes:

(a) pump means for pumping said diluted cleaning solution to said injection jet.

21. The system according to claim 20 wherein:

(a) said cleaning solution is drawn into said jet passage by venturi action.

22. A liquid waste disposal and canister flushing system for a canister having a lid with an accessory port, a base and a drain opening, which system comprises:

(a) a cabinet including a receptacle means for receiving at least a lower portion of the canister and the liquid waste contents thereof;

(b) drain valve means associated with said drain opening and having open and closed positions respectively opening and closing said drain opening;

(c) drain valve actuating means for opening said drain valve;

(d) an injection jet selectively received in said accessory port and including an upper end with an inlet port, a lower end with a discharge orifice and a jet passage extending between said inlet port and said discharge orifice, said discharge orifice being directed into said canister;

(e) a control system including means for supplying water to said injection jet water inlet port for a flush cycle comprising a predetermined duration; and (f) means for delaying the commencement of said flush cycle for a predetermined delay interval after the opening of said drain valve means.

23. The system according to claim 22, which includes:

(a) said cabinet having a lid with an open position exposing said sink and a closed position enclosing said sink; and (b) said control system being connected to said lid for controlling the operation of said system in response to the open or closed position of said lid.

24. A liquid waste disposal and canister flushing system for a canister having a lid with an accessory port, a base and a drain opening, which system comprises:

(a) a cabinet including a receptacle means for receiving at least a lower portion of the canister and the liquid waste contents thereof;

(b) drain valve means associated with said drain opening and having open and closed positions respectively opening and closing said drain opening;

(c) drain valve actuating means for opening said drain valve;

(d) an injection jet selectively received in said accessory port and including an upper end with an inlet port, a lower end with a discharge orifice and a jet passage extending between said inlet port and said discharge orifice, said discharge orifice being directed into said canister;

(e) said canister base has a configuration which is concave from an interior of said canister and includes said drain opening therein;

(f) said canister includes an annular lip projecting downwardly from said base;

(g) said lip includes a lower edge; and (h) said lip includes a drain notch extending from its lower edge to said canister base.

25. A method of disposing liquid waste from a canister having a lid with an accessory port, a base with a drain opening and a canister sidewall connected to the canister lid and canister base, which comprises the steps of:

a) providing the canister with a drain valve closing the drain opening;

b) opening the drain valve;

c) draining the canister liquid waste contents;

d) flushing the canister;

e) delaying the step of flushing the canister a predetermined length of time after commencing the step of draining the canister;

f) providing a cabinet with a receptacle;

g) placing at least a lower portion of the canister in the receptacle;

h) draining the canister liquid waste contents into the receptacle;

i) providing the cabinet with a sink having a sink floor;

j) providing the cabinet with a subsink having a mouth open at the sink floor and a subsink bottom positioned in spaced relation below the sink floor;

k) providing a drain line from said subsink bottom;

l) placing a lower portion of said canister in said subsink with said canister base positioned in spaced relation above said subsink bottom;

m) draining the canister liquid waste contents into the subsink; and n) draining the canister liquid waste contents from the subsink into the drain line.

26. The method according to claim 25, which includes the additional steps of:

a) providing a drain opening in said subsink bottom with a diameter equal to or greater than a diameter of said drain opening in said canister base; and b) draining the liquid waste from said subsink at a flow rate substantially equal to a flow rate of liquid waste drainage from said canister.

27. A method of disposing liquid waste from a canister having a lid with an accessory port, a base with a drain opening and a canister sidewall connected to the canister lid and canister base, which comprises the steps of:

a) providing the canister with a drain valve closing the drain opening;

b) opening the drain valve;

c) draining the canister liquid waste contents;

d) flushing the canister;

e) delaying the step of flushing the canister a predetermined length of time after commencing the step of draining the canister;

f) providing a water source;

g) providing an injection jet with a water inlet port and a discharge orifice;

h) providing a water inlet line;

i) connecting the water inlet line to the water source and to the injection jet water inlet port;

j) inserting the injection jet into the canister accessory opening;

k) providing a water stream from said water source through said water line, through said injection jet and out of said discharge orifice into said canister;

l) providing the drain valve with a stopper positioned in the drain opening with the drain valve closed;

m) providing a plunger rod with a lower end connected to the stopper and an upper end positioned in the accessory opening with the drain valve closed; and n) engaging said rod upper end with said injection jet, pushing said rod downwardly and ejecting said stopper from said drain opening as said injection jet is inserted in said accessory opening.

28. A method of disposing liquid waste from a canister having a lid with an accessory port, a base with a drain opening and a canister sidewall connected to the canister lid and canister base, which comprises the steps of:

a) providing the canister with a drain valve closing the drain opening;

b) opening the drain valve;

c) draining the canister liquid waste contents;

d) flushing the canister;

e) delaying the step of flushing the canister a predetermined length of time after commencing the step of draining the canister;

f) providing a water source;

g) providing an injection jet with a water inlet port and a discharge orifice;

h) providing a water inlet line;

i) connecting the water inlet line to the water source and to the injection jet water inlet port;

j) inserting the injection jet into the canister accessory opening;

k) providing a water stream from said water source through said water line, through said injection jet and out of said discharge orifice into said canister;

l) providing a cleaning solution source;

m) providing a cleaning solution inlet port in said injection jet;

n) providing a jet passage extending from said water inlet port to said discharge orifice;

o) providing a cleaning solution passage in said injection jet from said cleaning solution inlet port to said jet passage;

p) providing a cleaning solution line;

q) connecting said cleaning solution line to said cleaning solution source and to said cleaning solution inlet port;

r) drawing cleaning solution through said cleaning solution passage and into said jet passage by venturi action during a flush cycle; and s) discharging from said discharge orifice a diluted solution mixture of cleaning solution and water.

29. The method according to claim 28, which includes the additional steps of:

a) providing said injection jet with a generally cylindrical body having upper and lower ends and a longitudinal axis extending therebetween;

b) locating said water inlet port off-center at said upper end;

c) locating said discharge orifice off-center at said lower end; and d) extending said jet passage at a skewed angle with respect to said longitudinal axis between said water inlet port and said discharge orifice.

30. A method of disposing liquid waste from a canister having a lid with an accessory port, a base with a drain opening and a canister sidewall connected to the canister lid and canister base, which comprises the steps of:

a) providing the canister with a drain valve closing the drain opening;

b) opening the drain valve;

c) draining the canister liquid waste contents;

d) flushing the canister;

e) delaying the step of flushing the canister a predetermined length of time after commencing the step of draining the canister;

f) providing a water source;

g) providing an injection jet with a water inlet port and a discharge orifice;

h) providing a water inlet line;

i) connecting the water inlet line to the water source and to the injection jet water inlet port;

j) inserting the injection jet into the canister accessory opening;

k) providing a water stream from said water source through said water line, through said injection jet and out of said discharge orifice into said canister;

l) providing a control system with a microprocessor; and m) programming the microprocessor with a delay interval corresponding to a drain cycle with said drain valve open for a predetermined time limit prior to commencing the flush cycle.

31. The method according to claim 30, which includes the additional steps of:

a) programming said microprocessor with a flush cycle duration; and b) providing indicator means for indicating the completion of said flush cycle.

32. The method according to claim 30, which includes the additional steps of:

a) providing said control system with a speech synthesis output subsystem; and b) communicating said flush cycle completion with said speech synthesis subsystem.

33. The method according to claim 30, which includes the additional steps of:

a) providing said cabinet with a lid; and b) providing said control system with means for preventing the commencement of said flush cycle with said lid open.

34. A method of disposing liquid waste from a canister having a lid with an accessory port, a base with a drain opening and a canister sidewall connected to the canister lid and canister base, which comprises the steps of:

a) providing the canister with a drain valve closing the drain opening;

b) opening the drain valve;

c) draining the canister liquid waste contents;

d) flushing the canister;

e) delaying the step of flushing the canister a predetermined length of time after commencing the step of draining the canister;

f) providing a water source;

g) providing an injection jet with a water inlet port and a discharge orifice;

h) providing a water inlet line;

i) connecting the water inlet line to the water source and to the injection jet water inlet port;

j) inserting the injection jet into the canister accessory opening;

k) providing a water stream from said water source through said water line, through said injection jet and out of said discharge orifice into said canister;

l) reusing said canister; and m) discarding said canister lid and said drain valve.

35. A liquid medical waste disposal and canister flushing system for a canister having a lid with an accessory port, a base and a drain opening, which system comprises:

(a) a cabinet including a receptacle sized to receive at least a lower portion of the canister and the liquid waste contents thereof;

(b) a plunger subassembly comprising:

(i) a drain valve stopper associated with said drain opening and having open and closed positions respectively opening and closing said drain opening; and (ii) a plunger subassembly rod having a lower end connected to said stopper and an upper end extending into said accessory port; and (c) an injection jet selectively received in said accessory port and including an upper end with an inlet port, a lower end with a discharge orifice and a jet passage extending between said inlet port and said discharge orifice, said discharge orifice being directed into said canister.

36. The system according to claim 35, which includes:

(a) said plunger subassembly rod upper end being positioned in said canister lid accessory port with said valve means in its closed position and being engagable by said injection jet for opening said drain valve means.

* * * * *